(12) United States Patent
Frank et al.

(10) Patent No.: US 10,092,451 B2
(45) Date of Patent: Oct. 9, 2018

(54) GOGGLES

(71) Applicant: UVEX ARBEITSSCHUTZ GMBH, Fürth (DE)

(72) Inventors: Harald Frank, Nürnberg (DE); Michael Brandis, Nürnberg (DE); Johannes Kailas, Fürth (DE); Manfred Täuber, Langenzenn (DE)

(73) Assignee: UVEX ARBEITSSCHUTZ GMBH, Fürth (DE)

( * ) Notice: Subject to any disclaimer, the term of this patent is extended or adjusted under 35 U.S.C. 154(b) by 214 days.

(21) Appl. No.: 15/116,578

(22) PCT Filed: Jan. 30, 2015

(86) PCT No.: PCT/EP2015/051992
§ 371 (c)(1),
(2) Date: Aug. 4, 2016

(87) PCT Pub. No.: WO2015/117903
PCT Pub. Date: Aug. 13, 2015

(65) Prior Publication Data
US 2016/0354249 A1    Dec. 8, 2016

(30) Foreign Application Priority Data
Feb. 4, 2014    (DE) .......................... 10 2014 201 968

(51) Int. Cl.
*A61F 9/02*    (2006.01)
(52) U.S. Cl.
CPC .............. *A61F 9/025* (2013.01); *A61F 9/026* (2013.01); *A61F 9/027* (2013.01)

(58) Field of Classification Search
CPC ........................................................ A61F 9/025
USPC ............................................................ 2/439
See application file for complete search history.

(56) References Cited

U.S. PATENT DOCUMENTS

| | | | |
|---|---|---|---|
| 7,604,346 | B2 | 10/2009 | Wang |
| 7,882,575 | B2 | 2/2011 | Wang-Lee |
| 8,601,617 | B1 | 12/2013 | Krnc |
| 2003/0019018 | A1 | 1/2003 | Markovitz |
| 2006/0143808 | A1 | 7/2006 | Canavan |
| 2007/0028371 | A1 | 2/2007 | Chiang |

(Continued)

*Primary Examiner* — Katherine Moran
(74) *Attorney, Agent, or Firm* — Browdy and Neimark, PLLC

(57) ABSTRACT

Goggles are providing having a lens arrangement having two side end regions, a frame, a head holding arrangement, and two coupling arrangements for the releasable connection thereof to one another. Each coupling arrangement includes a first coupling device arranged on the lens arrangement and a respective second coupling device, which is arranged on the head holding arrangement and has a head holding arrangement part receiver to partly receive the respective first coupling device and a pivotable holding body with a holding device. Each holding body and each first coupling device of the respective coupling arrangement, in the assembled state of the goggles, have an articulated connection to one another by at least one joint projection. Each coupling arrangement includes a third coupling device, which is arranged on the frame and has a frame part receiver to partly receive the respective first coupling device and a holding counter-projection associated with the respective holding device when the respective holding body is in its holding position.

21 Claims, 6 Drawing Sheets

(56) References Cited

U.S. PATENT DOCUMENTS

2009/0222979 A1 9/2009 Wang
2011/0032472 A1 2/2011 Lin

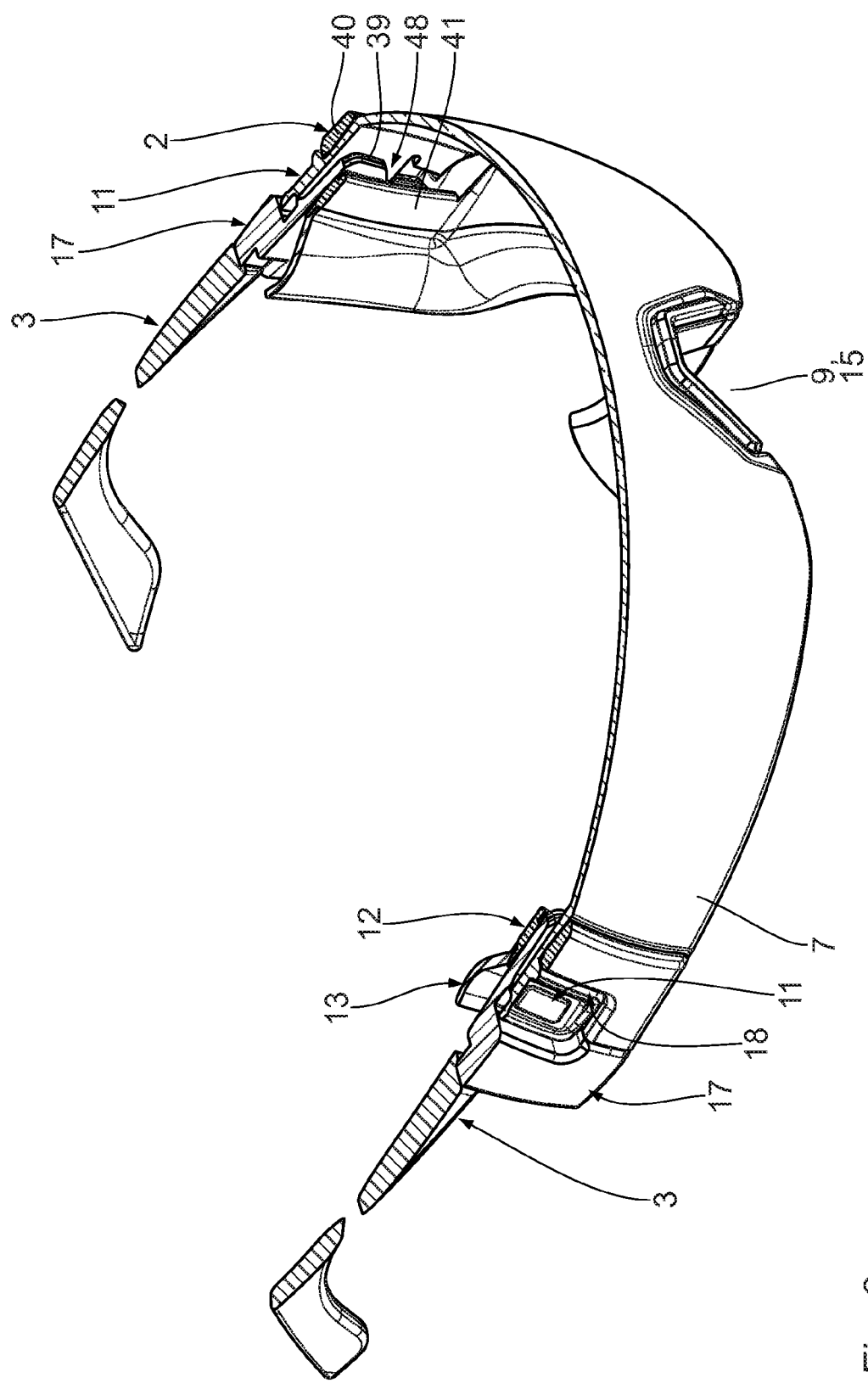

GOGGLES

CROSS-REFERENCE TO RELATED APPLICATIONS

This application claims the priority of German patent application 10 2014 201 968.0 filed on Feb. 4, 2014, the contents of which is incorporated herein by reference in its entirety as if fully set forth herein.

FIELD OF THE INVENTION

The invention relates to goggles, in particular work safety goggles. Alternatively, the goggles are, for example, configured as sports goggles.

BACKGROUND OF THE INVENTION

Multi-part goggles are already known from the prior art. The drawback in these known goggles is often that their assembly is time-consuming and complicated. In general, it is necessary to make the connection points between the individual components of the goggles extremely stable and solid.

Goggles disclosed in US 2003/0019018 A1 have a frame, two lens assemblies and a strap. The frame comprises lateral clips having outer notches and inner detents. The first lens assembly has side tabs with outer detents and inner notches. It is secured to the frame by inserting its side tabs into the clips until at least one of the notches is in engagement with the respective inner detent. By selecting the respective notch, the first lens assembly is arrangeable in various positions in relation to the frame. The second lens assembly comprises side tabs having a detent and an inner notch. The side tabs of the second lens assembly are inserted into the clips via the side tabs of the first lens assembly. The inner notch of the second lens assembly is in engagement with one of the detents of the first lens assembly. The first and second lens assemblies are secured to the frame by means of clips of the strap. The clips of the strap are inserted into the clips of the frame via the side tabs of the first lens assembly if only one lens is used, or via the side tabs of the second lens assembly if both lenses are used.

A lens assembly known from US 2009/0222979 A1 comprises a lens, a rigid frame, a resilient frame and a strap having buckles arranged at the ends thereof. The lens has laterally protruding tabs with a protrusion. On its sides, the rigid frame has in each case one outer notch. The resilient frame has in each case one through-hole on each of its sides. Each buckle has an engaging member and an aperture. The engaging members are inserted into the through-holes while the apertures are penetrated by the protrusions.

US 2007/0028371 A1 discloses swimming goggles comprising a frame, a pad, lenses, a connecting portion, a fastening portion and a strap. A side cover surrounds fastening parts arranged on two frame parts. An adjusting portion is connectable to the respective fastening part. The strap is secured to the adjusting portions.

Various masks, on which different devices, such as a data transmission unit, a monocle, a lens or an earpiece can be fastened, are known, for example, from U.S. Pat. No. 8,601,617 B1.

U.S. Pat. No. 7,882,575 B2 discloses safety goggles with a lens, a frame and a headband.

SUMMARY OF THE INVENTION

An object of the invention is therefore to provide multi-part goggles, which are easy to assemble and/or disassemble. Furthermore, the goggles should, in particular, also be able to withstand great mechanical stress, which, in particular, also applies to the connection points between the individual components. Moreover, the goggles should also preferably have a delicate appearance and be visually appealing.

This object is achieved according to the invention by goggles, in particular work safety goggles, comprising a lens arrangement, which has two mutually opposing side end regions, a frame to carry the lens arrangement, a head holding arrangement to locally fix the goggles on a head of a wearer, and two coupling arrangements for the coupling, releasable connection of the lens arrangement, the frame and the head holding arrangement to one another, wherein each coupling arrangement comprises a first coupling device arranged adjacent to the respective side end region on the lens arrangement, a second coupling device, which is arranged on the head holding arrangement and which has a head holding arrangement part receiver to partly receive the respective first coupling device, and a holding body, which is pivotable between a holding position and a release position, a holding means, wherein each holding body and each first coupling device of the respective coupling arrangement, in the assembled state of the goggles, have an articulated connection to one another by means of at least one joint projection, which predetermines a joint axis for pivoting the respective holding body, wherein a region of the holding body to be actuated for disassembly is only accessible from an inside of the goggles, and a third coupling device arranged adjacent to the respective side end region on the frame, which device has a frame part receiver to partially receive the respective first coupling device, and has a holding counter-means, which is associated with the respective holding means, to hold together the respective second coupling device and third coupling device when the respective holding body is in its holding position. The core of the invention is that the goggles comprise various coupling devices for the coupling, releasable connection of the lens arrangement, the frame and the head holding arrangement. In each case arranged on the lens arrangement and the frame as well as the head holding arrangement are coupling devices, which form coupling arrangements to couple the latter. In the assembled state of the goggles, the second coupling device and third coupling device of the respective coupling arrangement are connected to one another in a coupling manner by means of the associated holding means and holding counter-means. The first coupling device has a coupling connection to the respective second coupling device and third coupling device.

The projecting region of the holding body to be actuated for disassembly is only accessible from the inside of the goggles. This is used, in particular, for safety, as an unintentional disassembly of the goggles, for example by an extraneous body impacting on the goggles from outside, is thus avoided.

The at least one joint projection is preferably configured as an elongate joint web. Alternatively or additionally, the latter is, for example, arranged on the respective first coupling device.

It is advantageous if the lens arrangement, the frame and the head holding arrangement, before they are assembled, are separate or separated parts or components of the goggles. They can thus be easily exchanged.

It is expedient if the lens arrangement has a single, continuous one-piece lens. Alternatively, two individual lenses are present, which are connected to one another, for example, by means of a bridge, a nose web or the like. The lens arrangement is preferably substantially dimensionally stable.

The frame is advantageously peripherally closed. The frame preferably extends at least along a part, preferably at least along a large part of a periphery, of the lens arrangement. The frame preferably carries at least one sealing element for tight abutment on the face of a wearer. The at least one sealing element is preferably soft or yielding.

The head holding arrangement is advantageously configured as a head holding band, which runs around the back of the head of a wearer during use. The head holding band is preferably elastic. Alternatively, the head holding arrangement is, for example, configured as an arm arrangement comprising two goggle arms. It is advantageous if the goggle arms can be folded in and out in a known manner.

It is advantageous if the first coupling devices are, in each case, configured in one piece and are formed from plastics material.

The second coupling devices are in each case advantageously configured in one piece and formed from plastics material. If the heading holding arrangement is configured as a head holding band, the head holding band is preferably guided through each second coupling device and configured in the manner of a loop there to locally fix the respective second coupling device. Other fastenings between the head holding band and the second coupling devices are alternatively possible.

The third coupling devices are preferably formed in one piece and made of plastics material. The third coupling devices are advantageously configured in one piece with the frame in each case.

It is advantageous if the goggles are symmetrical with respect to a centre plane or plane of symmetry.

The holding bodies preferably close the respective part receivers towards the centre plane of the goggles. The holding bodies may have one or more holding means.

The configuration in which in the assembled state of the goggles, the head holding arrangement part receiver and the frame part receiver of the respective coupling arrangement together form a total receiver to receive the respective first coupling device and together peripherally surround this first coupling device at least in regions, preferably substantially completely, leads to an extremely loadable and secure local fixing of the first coupling device in relation to the second coupling device and third coupling device of the respective coupling arrangement. The second coupling device and the third coupling device of the respective coupling arrangement are substantially non-movable with respect to one another in the assembled state of the goggles.

The holding projection of each of the first coupling devices projects laterally outwardly with respect to a centre plane of the goggles. It preferably forms a bar and is advantageously web-like. In the assembled state of the goggles, the projection interacts in a blocking manner with the third coupling device and prevents a separation of the lens arrangement from the respective third coupling device in the viewing direction of the goggles. The holding projection, in the assembled state of the goggles, is preferably located within the respective part receiver. The holding projection preferably does not project laterally outwardly in relation to the adjacent third coupling device in the assembled state of the goggles. In particular, the holding projection does not project over an imaginary outer lateral limiting face of the third coupling device in the assembled state of the goggles. The holding projection, in the assembled state of the goggles, preferably even ends slightly below the imaginary outer lateral limiting face of the third coupling device.

In another preferred embodiment, the holding projection and the holding means of the respective coupling arrangement, in the assembled state of the goggles, project in opposite directions with respect to a centre plane of the respective coupling arrangement. It is advantageous if the holding projection and the holding means of the respective coupling arrangement are arranged offset with respect to one another in the viewing direction of the goggles.

The configuration in which each first coupling device is substantially angular, preferably rectangular, in particular prevents a tilting of the second coupling device or third coupling device in relation to the first coupling device of the respective coupling arrangement. The (rect)angular configuration of the first coupling device is, in particular, provided in a plane parallel to the centre plane of the goggles. In this plane, the first coupling device has an, in particular, (rect)angular cross sectional face or contour, the corners preferably being able to be rounded. Instead of a rectangular configuration, the first coupling device may, however, be trapezoidal, triangular, pentagonal, hexagonal or the like and have a corresponding cross sectional face or contour. Alternatively, the first coupling device may also be, in particular, elliptical, oval, ovoid or the like and have a corresponding cross sectional face or contour. The first coupling device would accordingly thus preferably be non-round. Likewise, the first coupling device may, however, also, for example, be round and have a corresponding cross sectional face or contour. Combinations of said different configurations are also possible.

It is advantageous if the frame part receivers and the head holding arrangement part receivers are in each case adapted to the shape or contour of the respective first coupling device in order to, preferably, in each case allow a positive connection between the first coupling devices and the respective total receivers. If, therefore, the first coupling devices are in each case round, the head holding arrangement part receivers and frame part receivers are preferably, in each case, segment of a circle-shaped, preferably semi-circular.

Provided in the viewing direction of the goggles, the through-opening of each third coupling device, through which the first coupling device can be introduced into the part received and removed therefrom, virtually also forms an assembly or disassembly opening.

The configuration of the holding body such that it projects in the viewing direction of the goggles in relation to a front edge of the respective through-opening for the manual pivoting of the holding body into its release position allows a particularly smooth pivoting of the respective holding body. It is advantageous if the region of the holding body projecting in relation to the through-opening can easily be reached by hand. The configuration of each holding body as a spring holding body that is in the holding position in the free state leads to a coupling arrangement, which is extremely operationally safe or functionally safe. The holding body is, in particular, configured in such a way that, in the assembled state of the goggles, it automatically springs into its holding position. To transfer the respective holding body from its holding position into its release position, a corresponding adjusting force, in particular, is to be applied to the holding body counter to the spring force.

The inner arrangement of the respective holding means in the respective third coupling device in the assembled state of the goggles leads to an extremely protected arrangement of the corresponding holding means. It is in particular protected from mechanical stress in this manner. It is advantageous if the associated holding counter-means is also arranged protected on the inside on the respective third coupling device.

In particular, the holding face of each holding means facing an adjacently arranged region of the head holding arrangement for interaction with the third coupling device is elongate. This advantageously lies in a plane running perpendicularly or obliquely with respect to a plane of symmetry of the goggles.

In the assembled state of the goggles, the holding counter-face of each holding counter-means, said holding counter-face facing the associated holding face for interaction with this holding face, runs adjacently to the associated holding face and then preferably lies flat thereon.

The configuration in which the second coupling device and the first coupling device run spaced apart from one another in the region of the respective holding means in the assembled state of the goggles when the respective holding body is in its holding position allows a pivoting of the respective holding body towards the first coupling device that is arranged adjacently and, in particular, spaced apart in this region in order to reach the release position of the holding body.

The configuration in which in the assembled state of the goggles, the lens arrangement rests on the respective third coupling device at its side end regions, in regions on the inside, leads to an extremely functionally safe and operationally safe coupling arrangement. The lens arrangement and the third coupling devices are thus fixed with respect to one another.

The configuration in which the lens arrangement and the first coupling devices are connected to one another in one piece allows an extremely safe or loss-proof connection between the first coupling devices and the lens arrangement. Goggles of this type can be produced in an extremely assembly-friendly and economical manner.

Two preferred embodiments of the invention will be described below by way of example with reference to the accompanying drawings.

BRIEF DESCRIPTION OF THE DRAWINGS

FIG. 6 shows a sectional view of the assembled goggles shown in FIG. 5.

DESCRIPTION OF THE PREFERRED EMBODIMENTS

Figure 1:
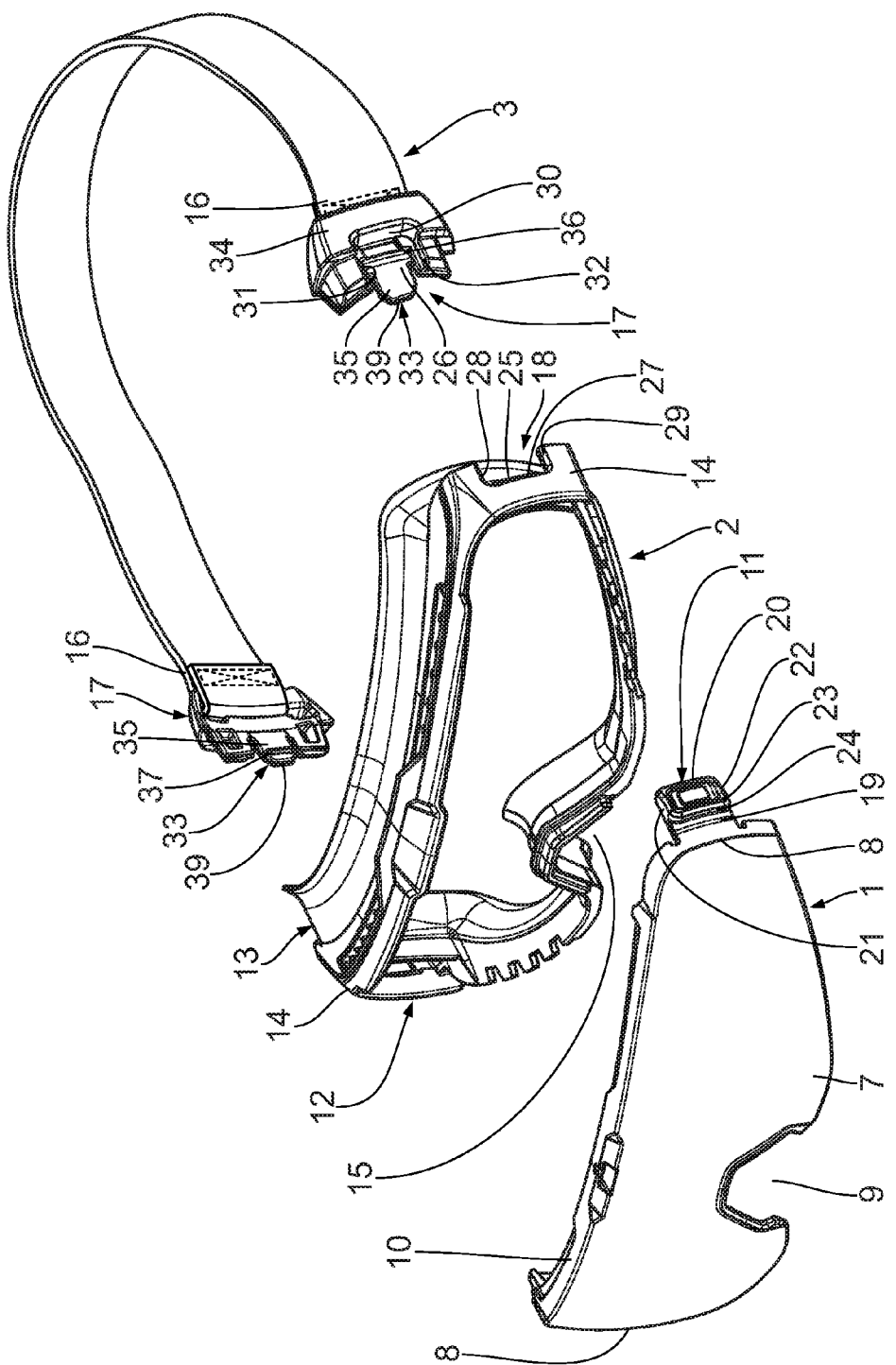
FIG. 1 shows an exploded view of goggles according to the invention according to a first embodiment.
Figure 2:
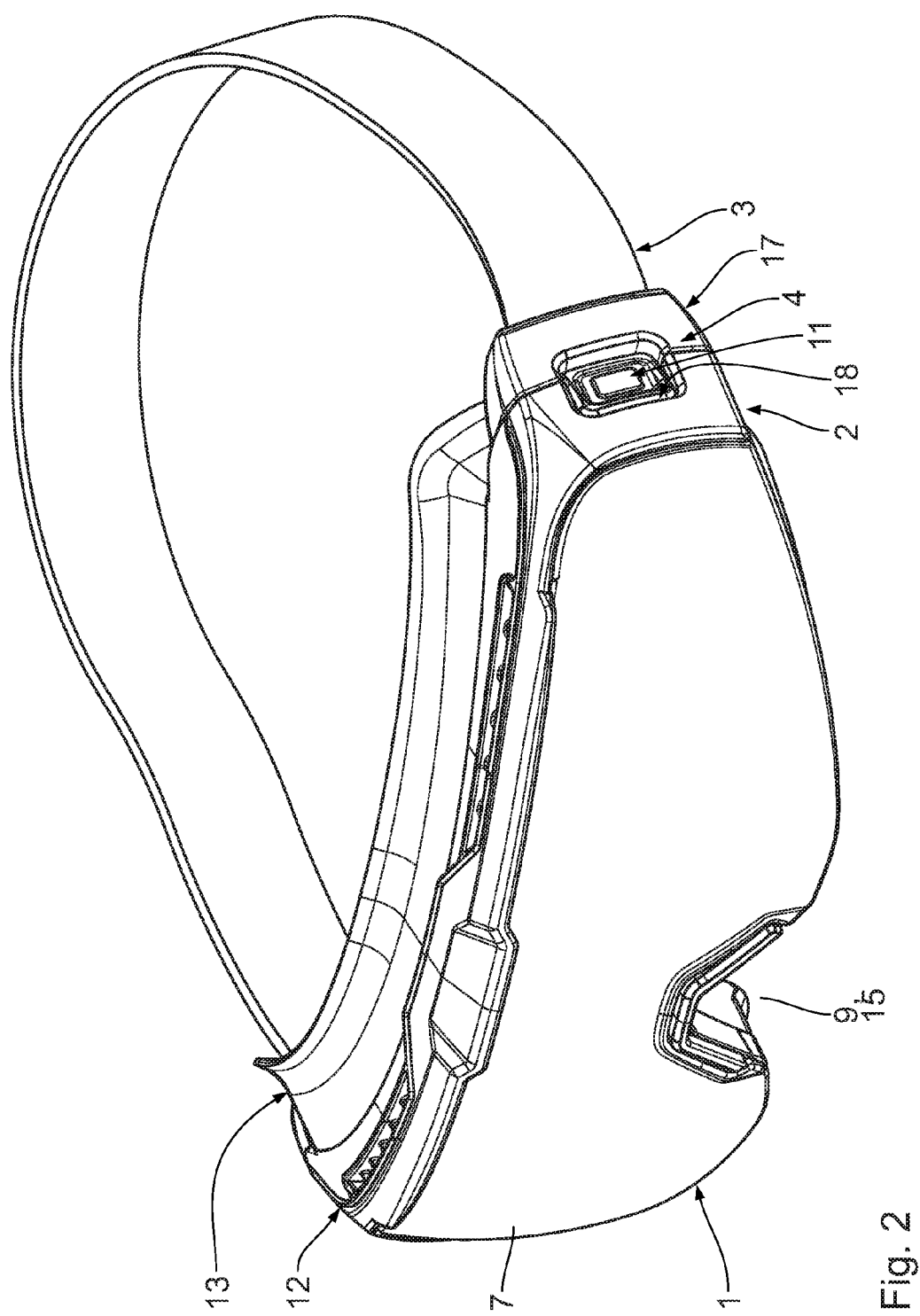
FIG. 2 shows a view which shows the goggles shown in FIG. 1 in the assembled or fitted state.
Figure 3:
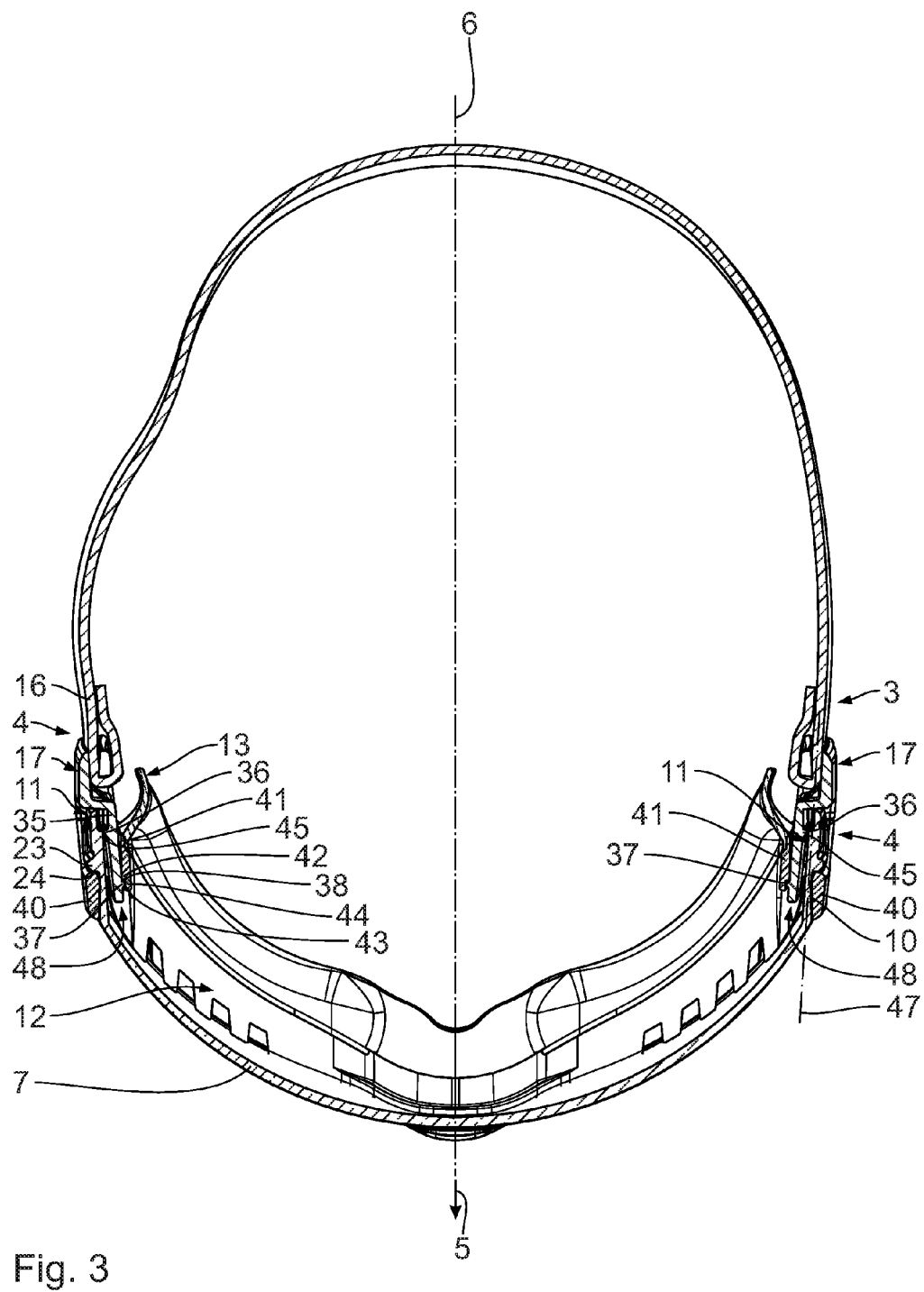
FIG. 3 shows a section through the assembled goggles illustrated in FIG. 2.
Figure 4:
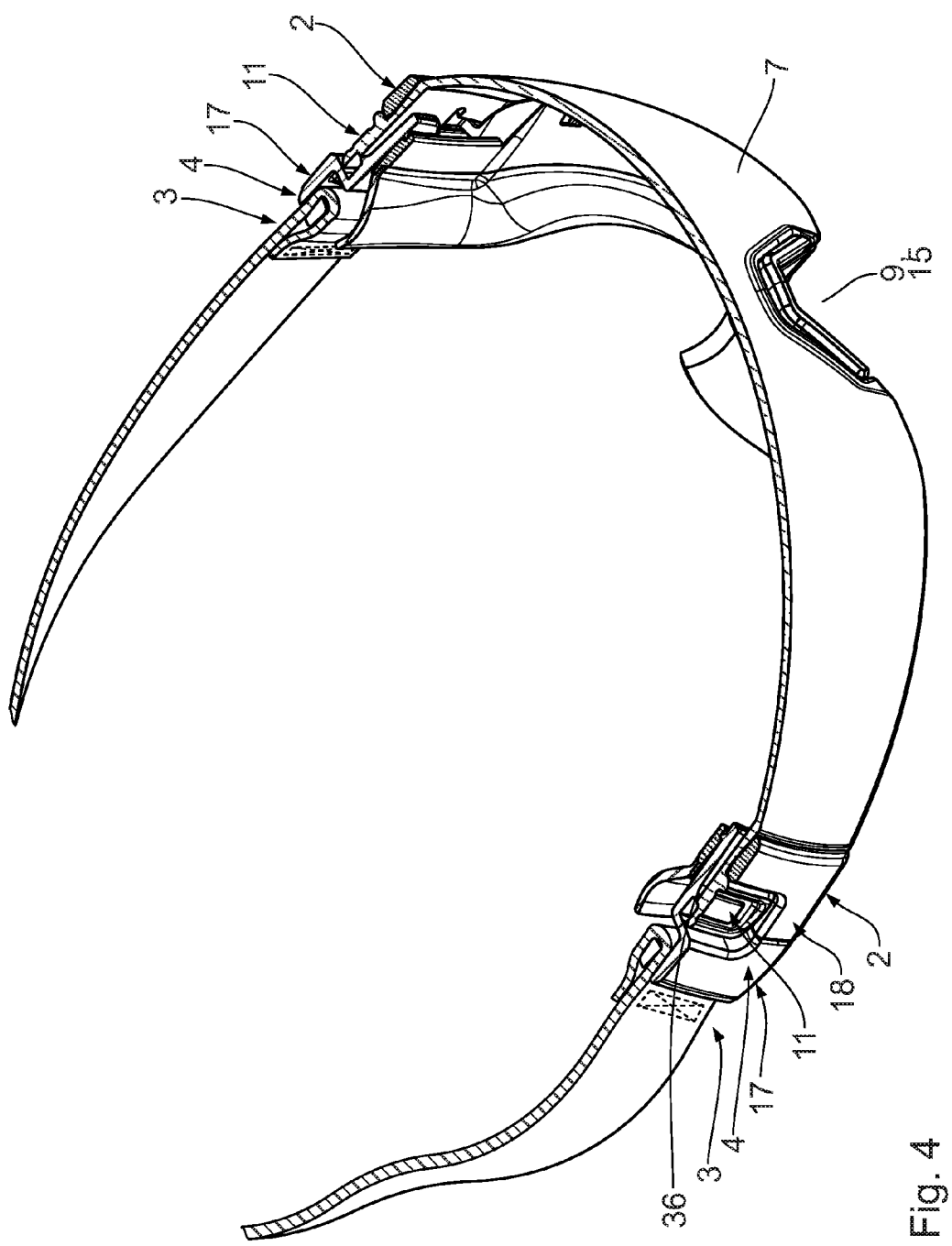
FIG. 4 shows a cut-away view of the assembled goggles shown in FIGS. 2 and 3.

Firstly, referring to the first embodiment shown in FIGS. 1 to 4, the goggles have a lens arrangement 1 and a frame 2 as well as a head holding arrangement 3. The lens arrangement 1, the frame 2 and the head holding arrangement 3 can be assembled to form the goggles and also separated from one another again. Two coupling arrangements 4 are provided for this, which are arranged laterally and are structurally identical.

When the goggles are worn correctly, these are situated in front of the eyes of the wearer and cover them. The goggles thus have a viewing direction 5. They are symmetrical with respect to a centre plane or plane of symmetry 6 extending in the viewing direction 5 and running centrally between the coupling arrangements 4.

The lens arrangement 1 comprises a single, continuous lens 7 and has two side end regions 8 opposing one another. Between the side end regions 8, the lens arrangement 1 has a nose recess 9 open at the bottom to receive a nose of a wearer. Adjoining the lens 7 is a connecting web 10, which runs around the entire lens 7 or along an edge region thereof and projects from the lens 7 counter to the viewing direction 5. In the assembled state of the goggles, the connecting web 10 engages in the frame 2, for example in a latching manner.

Adjoining each side end region 8 of the lens arrangement 1 is a first coupling device 11, which is configured substantially in the manner of a tab and projects from the lens arrangement 1 counter to the viewing direction 5.

The frame 2 is peripherally closed and has a basic shape, which in principle corresponds to the basic shape of the lens arrangement 1. It thus has two mutually opposing side end regions 14 and one nose recess 15, which is arranged centrally between them and is open at the bottom. The frame 2 is substantially formed from a dimensionally stable front frame part 12 in the viewing direction 5 and a rear sealing element 13, which is flexible or yielding and rests substantially tightly during use on the face of the wearer.

The head holding arrangement 3 is configured as a headband, which has two mutually opposing end regions 16.

A second coupling device 17 is fastened in each end region 16 of the headband. The second coupling arrangements 17 are arranged there in end loops of the headband. Furthermore, a third coupling device 18 is arranged in each side end region 14 of the frame 2. The third coupling devices 18 are rigidly connected to the frame 2.

The coupling devices 11, 17, 18, in the assembled state of the goggles have a positive connection to one another with the formation of the respective coupling arrangements 4. Since the coupling arrangements 4 are structurally identical, only one coupling arrangement 4 will mainly be dealt with below.

The first coupling devices 11 in each case adjoin the respective side end region 8 of the lens arrangement 1 by means of an elongate connection point 19. Opposite the respective connection point 19, each first coupling device 11 has a free rear support edge 20. An upper support edge 21 and a lower support edge 22 extend in each first coupling device 11 between the connection point 19 and the rear support edge 20. The upper support edge 21 and the lower support edge 22 of the respective first coupling device 11 run substantially parallel to one another and substantially perpendicular to the associated rear support edge 20 or the connection point 19.

Adjacent to the connection point 19, each first coupling device 11 has a holding projection 23, which runs parallel to the respective connection point 19. The holding projections 23 in each case project laterally outwardly in the manner of a bar in relation to the plane of symmetry 6. Each holding projection 23 has a bar face 24, which faces in the viewing direction 5 or forwards.

The first coupling devices 11, in the assembled state of the goggles, are in each case seated in part receivers 25, 26 of the second coupling device 17 or the third coupling device 18 of the respective coupling arrangement 4.

The part receivers 25, 26 of a coupling arrangement 4 together form a total receiver. The total receivers or part receivers 25, 26 are in each case laterally outwardly open with respect to the plane of symmetry 6. The part receivers 25 are in each case a component of the third coupling devices 18, while the part receivers 26 are in each case a component of the second coupling devices 17.

Each part receiver 25 is limited by a front limiting edge 27 in the viewing direction 5, an upper limiting part edge 28 and a lower limiting part edge 29. In relation to the front limiting edge 29, each part receiver 25 is open counter to the viewing direction 5. The upper limiting part edge 28 and the lower limiting part edge 29 of the respective part receiver 25 run substantially parallel to one another and substantially perpendicular to the front limiting edge 27.

Each part receiver 26 is limited by a rear limiting edge 30 in the viewing direction 5, an upper limiting part edge 31 and a lower limiting part edge 32. In relation to the rear limiting edge 30, each part receiver 26 is open in the viewing direction 5. The upper limiting part edge 31 and the lower limiting part edge 32 of the respective part receiver 26 run substantially parallel to one another and substantially perpendicular to the rear limiting edge 30.

The upper limiting part edges 28, 31 of the respective coupling arrangement 4, in the assembled state of the goggles, align with one another and together form an upper limiting edge. Likewise, the lower limiting part edges 29, 32 of the respective coupling arrangement 4, in the assembled state of the goggles, align with one another and together form a lower limiting edge.

The front limiting edge 27 and the rear limiting edge 30 of the respective coupling arrangement 4 run substantially parallel to one another and are arranged spaced apart from one another in the viewing direction 5. The part receivers 25, 26 of the respective coupling arrangement 4 are inwardly limited in each case towards the plane of symmetry 6 by a holding body 33, which is tab-like and a component of the second coupling device 17. Each holding body 33 is inwardly offset in relation to an outer face 34 of the second coupling device 17 with the formation of the respective rear limiting edge 30 and projects from there in the viewing direction 5. Each holding body 33 has a plate-like holding base 35 and a joint projection 36, which projects from the holding base 35 and is arranged adjacent to the respective rear limiting edge 30 and runs substantially parallel thereto. Each joint projection 36 projects outwardly from the associated holding base 35 in relation to the plane of symmetry 6 and in the process tapers. The joint projections 36 are web-like.

Furthermore, each holding body 33 has a holding means 37, which runs substantially parallel to the respective joint projection 36 of the coupling arrangement 4 and projects inwardly from the respective holding base 35 towards the plane of symmetry 6 with the formation of a respective holding face 38. It is advantageous for assembly reasons if each holding means 37 is ramp-like and rises counter to the viewing direction 5. The holding means 37 are arranged adjacent to, but spaced apart from, a free edge 39 of the respective holding body 33. The joint projection 36 and the holding means 37 of the respective coupling arrangement 4 thus project in opposite directions to each other from the respective holding base 35.

Each third coupling device 18 has an outer part 40 and an inner part 41 that is arranged adjacent thereto, but spaced apart therefrom. The outer parts 40 and the inner parts 41 are arranged or configured correspondingly on the frame 2. The part receivers 25 are arranged in the outer parts 40.

A holding counter-means 42 with a holding counter-face 43, which is formed by a counter-projection 44 projecting outwardly from the inner part 41 towards the associated outer part 40, is arranged on each inner part 41.

Each third coupling device has a through-opening 48, which is laterally limited by the respective outer part 40 and inner part 41. The through-openings 48 adjoin the respective part receiver 25 and are open in the viewing direction 5.

In the assembled state of the goggles, the lower support edges 22 of the first coupling devices 11 rest on the lower limiting edges of the total receivers, at least in regions, while the upper support edges 21 of the first coupling devices 11 rest, at least in regions, on the upper limiting edges of the total receivers. Furthermore, the rear support edges 20 rest, at least in regions, on the rear limiting edges 30. The holding projections 23 in each case rest, at least in regions, on the front limiting edges 27. In particular, the bar faces 24 rest in a locking manner on the front limiting edges 27, at least in regions. The joint projections 36 rest on the inside on the first coupling devices 11 with the formation of joint axes 45. The holding means 37 are connected or in contact with the associated holding counter-means 42. In particular, the holding faces 38 rest flat on the holding counter-faces 43 of the respective coupling arrangement 4, at least in regions.

Each joint axis 45 preferably runs substantially in a centre plane 47 of the respective coupling arrangement 4 or parallel thereto. Each joint axis 45 runs substantially parallel to the plane of symmetry 6. Each joint axis 45 runs substantially perpendicular to the viewing direction 5.

Due to the first coupling devices 11 being received in the second coupling devices 17 and third coupling devices 18 and due to the holding projections 23 resting on the third coupling devices 18, the first coupling devices 11 are locally fixed in relation to the second coupling devices 17 and third coupling devices 18 of the respective coupling arrangement 4. Due to the locking interaction between the holding means 37 and the holding counter-means 42 of the respective coupling arrangement 4, the second coupling devices 17 and the third coupling devices 18 of the respective coupling arrangement 4 are fixed in relation to one another. The holding bodies 33 are thus in their holding position.

The assembly of the goggles will be described below. Firstly, the second coupling devices 17 are inserted into the third coupling devices 18 in the viewing direction 5. The holding bodies 33 then spring outwardly into their holding position when their holding means 37 interact with the respective holding counter-means 42. The first coupling devices 11 are then joined counter to the viewing direction 5 by the third coupling devices 18 or the through-openings 48 in such a way that the first coupling devices 11 are located in the total receivers of the respective coupling arrangement 4.

Alternatively, the first coupling devices 11 are firstly inserted by the third coupling devices 18 counter to the viewing direction 5 into the part receiver 25 of the respective coupling arrangement 4. The second coupling devices 17 are then brought into latching connection with the third coupling devices 18.

To disassemble the goggles, the holding bodies 33 are pivoted laterally outwardly into their outer release position by applying a corresponding pivoting force at their free edge 39, so the latching connection between the holding means 37 and the associated holding counter-means 42 is released and a separation of the second coupling devices 17 and third coupling devices 18 of the respective coupling arrangement 4 is possible. The first coupling devices 11 are then guided out of the third coupling devices 18.

Figure 5:
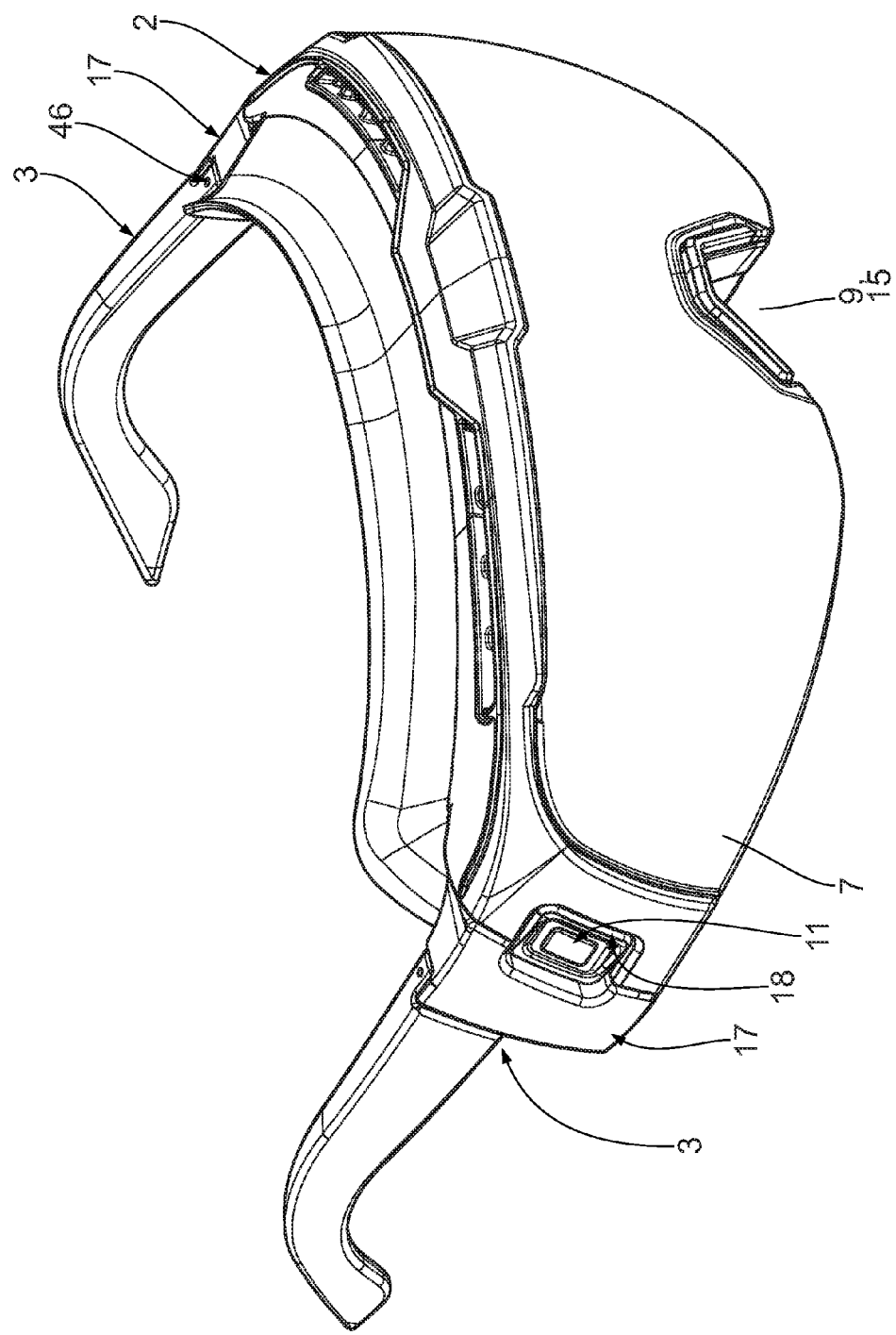
FIG. 5 shows a perspective view of goggles according to the invention in the assembled state according to a second embodiment.

The second embodiment will be described below with reference to FIGS. 5 and 6. In contrast to the previous embodiment, to the description of which reference is made, the head holding arrangement 3 is formed by two goggle arms, which can be folded in and out by a hinge arrangement 46. Otherwise there are no differences.

The invention claimed is:

1. Goggles,
   a) with a lens arrangement, which
      i) has two mutually opposing side end regions,
   b) with a frame to carry the lens arrangement,
   c) with a head holding arrangement to locally fix the goggles on a head of a wearer, and
   d) with two coupling arrangements for a coupling, releasable connection of the lens arrangement, the frame and the head holding arrangement to one another, wherein each coupling arrangement comprises
      i) a first coupling device arranged adjacent to the respective side end region on the lens arrangement,
      ii) a second coupling device, which is arranged on the head holding arrangement and which
      has a head holding arrangement part receiver to partly receive the respective first coupling device, and
      a holding body, which is pivotable between a holding position and a release position, with a holding device, wherein each holding body and each first coupling device of the respective coupling arrangement, in the assembled state of the goggles, have an articulated connection to one another by at least one joint projection, which predetermines a joint axis for pivoting the respective holding body,
      wherein a region of the holding body to be actuated for disassembly is only accessible from an inside of the goggles, and
      iii) a third coupling device arranged adjacent to the respective side end region on the frame, the third coupling device
      having a frame part receiver to partially receive the respective first coupling device, and
      having a holding counter-element, which is associated with the respective holding device, to hold together the respective second coupling device and third coupling device when the respective holding body is in its holding position.

2. Goggles according to claim 1, wherein the goggles are work safety goggles.

3. Goggles according to claim 1, wherein, in the assembled state of the goggles, the head holding arrangement part receiver and the frame part receiver of the respective coupling arrangement together form a total receiver to receive the respective first coupling device and together peripherally surround this first coupling device at least in regions.

4. Goggles according to claim 3, wherein, in the assembled state of the goggles, the head holding arrangement part receiver and the frame part receiver together peripherally surround the first coupling device substantially completely.

5. Goggles according to claim 3, wherein, in the assembled state of the goggles, each first coupling device has a positive connection to the associated total receiver.

6. Goggles according to claim 1, wherein each first coupling device has a holding projection projecting laterally outwardly with respect to a centre plane of the goggles, the projection, in the assembled state of the goggles, interacting in a blocking manner with the third coupling device and preventing a separation of the lens arrangement from the respective third coupling device in a viewing direction of the goggles.

7. Goggles according to claim 6, wherein the holding projection and the holding element of the respective coupling arrangement, in the assembled state of the goggles, project in opposite directions with respect to a center plane of the respective coupling arrangement.

8. Goggles according to claim 1, wherein each first coupling device is substantially angular.

9. Goggles according to claim 8, wherein each first coupling device is substantially rectangular.

10. Goggles according to claim 1, wherein each third coupling device has a through-opening in a viewing direction of the goggles, through which the first coupling device is introducible into the part receiver and removable therefrom.

11. Goggles according to claim 10, wherein each holding body projects in the viewing direction of the goggles in relation to a front edge of the respective through-opening for the manual pivoting of the holding body into its release position.

12. Goggles according to claim 1, wherein each holding body is configured as a spring holding body and is in the holding position in the free state.

13. Goggles according to claim 1, wherein the at least one joint projection is arranged on the respective holding body.

14. Goggles according to claim 1, wherein, in the assembled state of the goggles, each holding element is received within the respective third coupling device.

15. Goggles according to claim 1, wherein each holding element projects in relation to a holding base of the respective holding body with a formation of a holding face facing an adjacently arranged region of the head holding arrangement for interaction with the third coupling device.

16. Goggles according to claim 15, wherein each holding element projects inwardly towards a center plane of the goggles in relation to said holding base of the respective holding body.

17. Goggles according to claim 15, wherein each holding counter-element is configured as a holding counter-projection, which, in the assembled state of the goggles, has a holding counter-face facing the associated holding face for interaction with the holding face.

18. Goggles according to claim 1, wherein the second coupling device and the first coupling device run spaced apart from one another in the region of the respective holding device in the assembled state of the goggles when the respective holding body is in a holding position.

19. Goggles according to claim 1, wherein, in the assembled state of the goggles, the lens arrangement at its side end regions, in regions on the inside, rests on the respective third coupling device.

20. Goggles according to claim 1, wherein the lens arrangement and the first coupling devices are connected to one another in one piece.

21. Goggles according to claim 1, wherein each joint projection is configured as an elongate joint web.

* * * * *